(12) United States Patent
Ashe

(10) Patent No.: US 6,691,897 B2
(45) Date of Patent: Feb. 17, 2004

(54) SANITIZING STAND AND METHOD FOR DISPENSING FREE PUBLIC HEALTH CLEANING AND SANITIZING SUPPLIES

(75) Inventor: Jason C. Ashe, Clackamas, OR (US)

(73) Assignee: Jason Ashe, Clackamas, OR (US)

( * ) Notice: Subject to any disclaimer, the term of this patent is extended or adjusted under 35 U.S.C. 154(b) by 1 day.

(21) Appl. No.: 10/125,733

(22) Filed: Apr. 17, 2002

(65) Prior Publication Data

US 2003/0197026 A1 Oct. 23, 2003

(51) Int. Cl.[7] .................................................. B67D 5/64
(52) U.S. Cl. ...................... 222/174; 222/192; 221/96; 221/199; 248/146; 248/905; 248/907
(58) Field of Search ................................ 222/174, 192; 221/96, 199; 248/140, 905, 907

(56) References Cited

U.S. PATENT DOCUMENTS

| 4,143,792 A | * | 3/1979 | Rex | ............................. 221/199 |
| 5,312,021 A | * | 5/1994 | Nelson | ........................ 222/192 |
| 6,170,692 B1 | * | 1/2001 | Johnston | |

* cited by examiner

Primary Examiner—Philippe Derakshani
(74) Attorney, Agent, or Firm—Donald W. Meeker

(57) ABSTRACT

A pole on a base has mounted containers for freely dispensing antibacterial hand cleaner, sanitizing spray, disposable towels and other cleaning and sanitizing supplies. A waste disposal container rests on the flat base and is clipped to the pole. An information display, preferably visible from all sides, is mounted at the top of the pole at eye level. Triagulated print or lighted slide panels or animated screen displays and sound could be used for advertising and information. Selling or renting advertising space pays for the free dispensing of sanitizing supplies for public health.

18 Claims, 1 Drawing Sheet

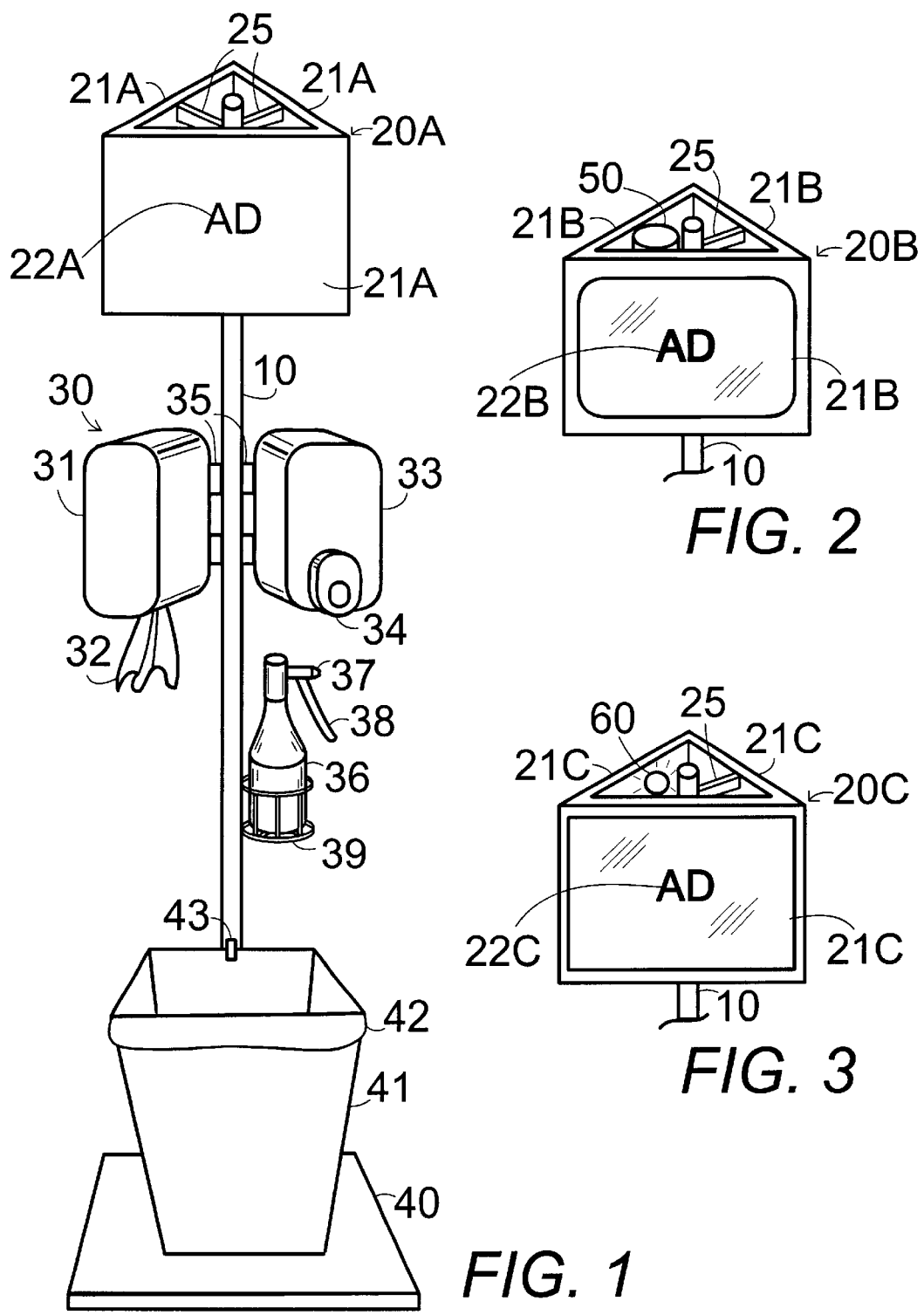

SANITIZING STAND AND METHOD FOR DISPENSING FREE PUBLIC HEALTH CLEANING AND SANITIZING SUPPLIES

BACKGROUND OF THE INVENTION

1. Field of the Invention

The present invention relates to cleaning, maintenance and sanitizing and public health and in particular to a sanitizing station equipped with containers for freely dispensing wiping and sanitizing means to clean and sanitize shared facilities and equipment and the user's hands, and an eye-level advertising and information display, the sanitizing station having a stand-alone supported pole and being positionable in central locations adjacent to shared facilities where cleaning and sanitizing supplies are needed for public health, the advertising media subsidizing the public health benefits of the supplies.

2. Description of the Prior Art

Public health is a major concern in all countries and all locations within countries. Interaction between people presents opportunities to spread communicable diseases and ailments. Providing public cleaning and sanitizing supplies to maintain public health can be a very costly measure which is seldom provided for. Even within facilities run commercially and even those facilities with laws regulating the health standards, because of costs and profit considerations public health needs are almost never met satisfactorily. While cleaning and sanitizing means have been developed to solve public health problems they are very seldom provided simply due to cost factors.

Public gathering places are a breeding ground for communicable diseases and common ailments such as colds and flu. Such locations, especially those with equipment being handled by large numbers of people, include: casinos with slot machines, restaurants with eating utensils, tables, countertops and chairs, arcades with games, fairs with amusements, amusement parks, concerts and other outdoor events with portapotties, child care facilities with toys and many other such public facilities with rest rooms, hospitals, and athletic facilities being particularly notable.

Athletic facilities such as gyms and health clubs are a prime breeding ground for germs of all kinds. Because of the nature of athletic facilities, sweat is everywhere. People sweat while using equipment and leave a good amount of that sweat on the equipment. People are generally sweaty while moving about the facility and leave traces of that sweat everywhere the sweaty person walks, jogs, or sits and on every piece of furniture and equipment used by the sweaty person.

The next person using the athletic equipment naturally comes in contact with the sweat of the previous person because of having to grip the equipment, sit, lay or stand on it in the same way as the previous sweaty user.

In addition to being unsavory in general to contact other peoples' sweat, it is a breeding ground and potential transmitter of disease. From contact of the equipment, there is a very real danger of contracting a cold, flu, or other more serious diseases, such as AIDS which is transmitted by body fluids, such as blood which might also be present due to injuries, broken blisters, cuts and scratches or for other reasons.

Furthermore, companies are always desirous of being able to provide advertisements and service announcements about products, services, events, and other information useful to the large numbers of people gathering in public use facilities. The affluent users of athletic facilities are a prime example.

While there have been other attempts to solve equipment contact problems and sanitizing problems, none address the situation effectively of providing a realistic reasonable cost way to clean and sanitize equipment after or before every use of the equipment. Attendants are simply not able to keep up with that task. And advertising and announcement means are often limited to small bulletin boards in inconspicuous places within such facilities.

U.S. Pat. No. 5,817,379, issued Oct. 6, 1998 to Rich, describes a two-sided towel for wiping moisture from two different surfaces while preventing cross contamination of the moisture between the surfaces. Coextensive first and second sheets, each having a moisture absorbent side and a moisture impervious side are fastened together with the moisture impervious sides abutting. The edges of the resulting sandwich are fastened together while leaving at least a portion of one edge unfastened, forming a pocket between the sheets into which a hand can be inserted. Typically, the towel is used by a fitness center patron to wipe perspiration from his or her body with one side and wipe moisture and dirt from equipment with the other side. The towel can also have fasteners to release close the opening so that it can be used as a bag, or be turned inside out and closed to carry damp clothing inside.

U.S. Pat. No. 6,220,997, issued Apr. 24, 2001 to Kohl, claims an exercise equipment prophylactic covering system, for use in preventing bodily contact with exercise equipment, and thereby preventing contact with bodily fluids from previous users of said exercise equipment. The system includes a seat cover, a single open ended tubular cover, a double open ended tubular cover, and a bicycle handle bar cover. The seat cover is preferably used on any type of seat, said cover attaching over the top of the seat back. The double open ended tubular cover is preferably used on any bar which does not have an open end or forms a continuous part of an exercise machine, such as the handle bars on step machines and the like. The single open ended tubular cover is preferably used on any equipment which provides an open ended handgrip, such as a pull down bar, dumbbells, barbells, and the like. The bicycle handle bar cover secures over the handle bars of a spinning bicycle.

U.S. Pat. No. 6,357,616, issued Mar. 19, 2002 to Harris, shows an attachable holder for exercise devices including a housing having an open upper end a closed lower end. The closed lower end has an elongated recess formed therein. The elongated recess is dimensioned for receiving the horizontal support bar of the piece of equipment therein. The closed lower end has a cover member hingedly coupled thereto. The cover member has a closed orientation containing the horizontal support bar within the elongated recess.

U.S. Pat. No. 5,803,249, issued Sep. 8, 1998 to Harsanyi, provides a medical clean up kit made up of a container with multiple compartments for storing the clean up material. A first compartment dispensively houses a supply of moistened towelettes saturated with anti-pathogenic agents for destroying various viruses and bacteria. A second compartment dispensively houses a supply of dry towelettes. Various lids and closures are disclosed for sealing the compartments, and preventing the accidental spillage of anti-pathogenic agents which might precipitate from the moist towelettes.

U.S. Pat. No. 5,732,422, issued Mar. 31, 1998 to McAllister, indicates a combination hand sink and trash receptacle comprises a hand sink having a horizontal support surface and a wash basin downwardly extending from the support surface. A fixed trash skirt is positioned around the wash basin, and the skirt is secured to the underside of the horizontal support surface. The trash skirt has a front face with a trash opening therein, and a movable trash receptacle is mounted directly under the trash skirt. A horizontal sliding connection between the fixed trash skirt and the movable trash receptacle includes horizontal side flanges on the trash receptacle and horizontal side channels on the trash skirt constructed and arranged to slidingly receive the side flanges on the trash receptacle.

U.S. Pat. No. 6,298,502, issued Oct. 9, 2001 to Brown, discloses a central steel column serves as a core module for a portable washstand. The column extends upwardly from a horizontal foot, and has foot pumps which communicate with a water intake tube and with water spigots. In addition, the central column has fasteners, such as adjustable bands, for connecting fresh and waste water receptacles to the column. The receptacles may be conventional cylindrical drums, which support a molded plastic countertop with washbasins positioned beneath the spigots. For decorative purposes, a molded front panel extends between the countertop and the base, and together with a sheet rear panel encloses the two drums. Paper towel and soap dispensers may be connected to the central column.

A need exists for a conveniently located reasonably priced system to satisfy the need for cleaning and sanitizing hands and shared facilities such as gaming devices, furniture, equipment and other things used in common, especially athletic equipment. A need to subsidize such public health solutions is paramount.

SUMMARY OF THE INVENTION

An object of the present invention is to provide a cleaning and sanitizing station for hands and shared facilities and equipment within easy access in centrally located positions in all public locations adjacent to the common use facilities and equipment.

Another object of the present invention is to provide drying and wiping means for equipment or personal use within easy access throughout a publicly used facility.

One more object of the present invention is to provide an antibacterial hand cleaner within easy access throughout a public facility.

A further object is to provide a waste disposal depository for properly disposing of wet, soiled and contaminated wiping means after use.

An additional object of the present invention is to provide a highly visible eye-level advertising medium in highly visible centrally located sanitizing stations in all heavily trafficked areas of public use facilities where cleaning and sanitizing materials are needed for public health, the advertising space being sold to subsidize the provision of public health supplies.

In brief a stand having a base supporting a pole is equipped to provide a public dispenser for sanitizing hands and equipment including disposable towels, cleaning and sanitizing supplies for equipment, and antibacterial hand cleaning supplies attached to the pole for easy free access, as well as a disposal container positioned on a base plate and secured to the pole with a clip to maintain a plastic trash bag in place within the disposal container.

A means for providing information such as an advertising or public announcement display is mounted at eye-level at the top of the pole with images visible from all sides of the pole. A three-panel triangulated mount or three screen triangulated mount are two possibilities for a sign or poster-type image on the panel and an animated display on the screens. The panels could be plain flat panels for mounting printed media, backlighted translucent screens for colorful transparent slides or other commonly used panel displays. The screens could be television screens, CRTs, digital display screens, or any other screen capable of animated displays. Both panels and screens could be supplemented by speakers producing sound as well.

An advantage of the present invention is that is satisfies the need for providing badly needed cleaning and sanitizing supplies in large quantities in highly used public locations with shared use facilities and equipment with the public health supplies freely dispensable by being subsidized by the sale or rent of advertising space on the standalone cleaning and sanitizing supply stand.

Another advantage of the present invention is that it solves the health and aesthetic problems of shared use of equipment to enable a complete wipe-down of the equipment and of the user's hands with sanitizing and antibacterial cleaning supplies and wipes which are disposed of properly at the same time.

An additional advantage of the present invention is that since the supplies are being dispensed for free there is less chance of the supply containers being vandalized, which happens with pay dispensers containing money.

BRIEF DESCRIPTION OF THE DRAWINGS

These and other details of my invention will be described in connection with the accompanying drawings, which are furnished only by way of illustration and not in limitation of the invention, and in which drawings:

FIG. 1 is a perspective view of the stand-alone sanitizing stand with top eye-level information/advertising display and a pole with containers for freely dispensing cleaning and sanitizing liquids, sprays and disposable wipes and including a waste disposal container clipped to the pole and resting on a base plate;

FIG. 2 is a perspective view of an alternate embodiment of the information display on the top of the sanitizing stand of FIG. 1 which comprises at least one and preferably three screens capable of animated images, and shows a speaker mounted behind the screens;

FIG. 3 is another alternate embodiment of the information display on the top of the sanitizing stand of FIG. 1 which comprises at least one and preferably three backlighted translucent screens, showing a light bulb mounted behind the screens.

BEST MODE FOR CARRYING OUT THE INVENTION

In FIGS. 1, 2, and 3 a stand for the free dispensing of cleaning and sanitizing supplies and for displaying information comprises a flat base plate 40 capable of supporting an upright element, a pole 10 permanently supported by the base with a conventional support means in a vertical upright position, an information display 20A, 20B, and 20C positioned adjacent to a top of the pole at eye level, attached to the pole by conventional bracket means 25, a number of free dispensers 30 including at least one wipe dispenser 31, permanently attached to the pole 10 by a conventional bracket means 35, for containing and freely dispensing at least one disposable wiping means 32 at a time, at least one sanitizing spray container 36 removably attached to the pole 10 as resting in a conventional holder 39 for freely dispensing a quantity of a sanitizing fluid through a nozzle 37 operated by a handle 38 for spraying common use facilities and equipment, at least one hand cleaning dispenser 33 permanently attached to the pole 10 by a conventional bracket 35 for freely dispensing a quantity of at least one hand cleaning substance such as through a liquid dispenser 34, and at least one waste disposal receptacle 41 resting on the base plate 40 and removably clipped to the pole 10 by a clip means 43, which could be spring-loaded clip or an upside-down hook, as a means to retain a waste disposal bag 42 inside the receptacle 41 and maintain the receptacle in an upright position.

The public health cleaning and dispensing containers 30 can be any of a variety of different types of dispensing containers dispensing any of a variety of cleaning, wiping and sanitizing means. In FIG. 1 the hand cleaning substance is preferably an antibacterial hand cleaner dispensed through the liquid dispenser 34 of the hand cleaning dispenser 33. The disposable wiping means comprises a paper towel 32 dispensed through the wipe dispenser 31. Preferably the disposable wiping means comprises a disposable towel 32 impregnated with an antibacterial agent. Another wipe means could be a personal paper tissue or a personal paper tissue impregnated with an antibacterial agent, or a moist towlette. The sanitizing spray container 36 removably attached to the pole 10 preferably comprises a spray bottle of sanitizing fluid for spraying equipment, such as athletic equipment or other entertainment or other devices in shared use.

The information display 20A, 20B, and 20C is capable of displaying at least one paid advertisement 22A, 22B, and 22C to subsidize the free dispensing of cleaning and sanitizing supplies for the benefit of public health and providing better service to customers for businesses. The information display comprises at least two panels, preferably three panels 21A permanently attached adjacent to a top of the pole by a conventional bracket means 25, with the three panels 21A interconnected in a triangular configuration end to end around the pole so that they are visible from all angles. In FIG. 1 the panels 21A comprise smooth panels for receiving printed media, such as a printed ad 22A mounted thereon.

In FIG. 2 the information display 20B comprises at least one and preferably three screens 21B capable of animated images, such as television screens, CRT (cathode ray tube) screens, digital display screens, or other animated display means showing animated ads 22B.

In FIG. 3 the information display comprises at least one and preferably three backlighted translucent screens 21B as by a light bulb 60 for receiving colorful transparent slides thereon preferably showing colorful ads 22C.

As seen in FIG. 2 the information display may further comprise a means for producing sound such as a speaker 50 which may be mounted behind the visual display.

In use, a method for dispensing free public health cleaning and sanitizing supplies and for displaying information comprises the step of creating a stand comprising a flat base plate 40 capable of supporting an upright element, a pole 10 permanently supported by the base in a vertical upright position, an information display 20A, 20B, and 20C positioned adjacent to a top of the pole at eye level, at least one wipe dispenser 31 permanently attached to the pole for containing and freely dispensing at least one disposable wiping means 32 at a time, at least one sanitizing spray container 36 removably attached to the pole for freely dispensing a quantity of a sanitizing fluid for spraying common use facilities and equipment, at least one hand cleaning dispenser 33 permanently attached to the pole for freely dispensing a quantity of at least one hand cleaning substance, and at least one waste disposal receptacle 41 resting on the base plate 40 and removably clipped to the pole by a clip means 43 to retain a waste disposal bag inside the receptacle and maintain the receptacle in an upright position, and the step of placing paid advertisements 22A, 22B, and 22C on the information display to pay for freely dispensing the public health cleaning and sanitizing supplies.

It is understood that the preceding description is given merely by way of illustration and not in limitation of the invention and that various modifications may be made thereto without departing from the spirit of the invention as claimed.

What is claimed is:

1. A stand for the free dispensing of cleaning and sanitizing supplies and for displaying information, the stand comprising:
    a flat base plate capable of supporting an upright element;
    a pole permanently supported by the base in a vertical upright position;
    an information display positioned adjacent to a top of the pole at eye level, the information display being capable of displaying at least one paid advertisement to subsidize the free dispensing of cleaning and sanitizing supplies;
    at least one wipe dispenser permanently attached to the pole for containing and freely dispensing at least one disposable wiping means at a time;
    at least one sanitizing spray container removably attached to the pole for freely dispensing a quantity of a sanitizing fluid for spraying common use facilities and equipment;
    at least one hand cleaning dispenser permanently attached to the pole for freely dispensing a quantity of at least one hand cleaning substance;
    at least one waste disposal receptacle resting on the base plate and removably clipped to the pole by a means to retain a waste disposal bag inside the receptacle and maintain the receptacle in an upright position.

2. The stand of claim 1 wherein the hand cleaning substance is an antibacterial hand cleaner.

3. The stand of claim 1 wherein the disposable wiping means comprises a paper towel.

4. The stand of claim 1 wherein the disposable wiping means comprises a disposable towel impregnated with an antibacterial agent.

5. The stand of claim 1 wherein the disposable wiping means comprises a personal paper tissue.

6. The stand of claim 1 wherein the disposable wiping means comprises a personal paper tissue impregnated with an antibacterial agent.

7. The stand of claim 1 wherein the disposable wiping means comprises a moist towlette.

8. The stand of claim 1 wherein the sanitizing spray container removably attached to the pole comprises a spray bottle of sanitizing fluid.

9. The stand of claim 1 wherein the information display comprises at least two panels permanently attached adjacent to a top of the pole.

10. The stand of claim 9 wherein the panels comprise smooth panels for receiving printed media mounted thereon.

11. The stand of claim 9 wherein the information display comprises three panels interconnected in a triangular configuration end to end around the pole.

12. The stand of claim 1 wherein the information display comprises at least one backlighted translucent screen for receiving colorful transparent slides thereon.

13. The stand of claim 1 wherein the information display comprises at least one television screen.

14. The stand of claim 1 wherein the information display comprises at least one CRT screen.

15. The stand of claim 1 wherein the information display comprises at least one digital display screen.

16. The stand of claim 1 wherein the information display comprises at least one screen capable of animated displays.

17. The stand of claim 1 wherein the information display further comprises a means for producing sound.

18. A method for dispensing free public health cleaning and sanitizing supplies and for displaying information, the method comprising:

the step of creating a stand comprising a flat base plate capable of supporting an upright element, a pole permanently supported by the base in a vertical upright position, an information display positioned adjacent to a top of the pole at eye level, at least one wipe dispenser permanently attached to the pole for containing and freely dispensing at least one disposable wiping means at a time, at least one sanitizing spray container removably attached to the pole for freely dispensing a quantity of a sanitizing fluid for spraying common use facilities and equipment, at least one hand cleaning dispenser permanently attached to the pole for freely dispensing a quantity of at least one hand cleaning substance, and at least one waste disposal receptacle resting on the base plate and removably clipped to the pole by a means to retain a waste disposal bag inside the receptacle and maintain the receptacle in an upright position;

the step of placing paid advertisements on the information display to pay for freely dispensing the public health cleaning and sanitizing supplies.

* * * * *